(12) United States Patent
Park et al.

(10) Patent No.: US 9,650,488 B2
(45) Date of Patent: May 16, 2017

(54) METHOD FOR BELCHING WATER FROM SWOLLEN SUPERABSORBENT POLYMERS AND METHOD FOR RECYCLING SANITARY ABSORBENT ARTICLES USING THE SAME

(71) Applicants: KIMBERLY-CLARK WORLDWIDE, INC., Neenah, WI (US); YUHAN-KIMBERLY, LIMITED, Seoul (KR)

(72) Inventors: Jik Hwan Park, Seoul (KR); Jea Seung Chin, Suwon-Si (KR); Ho Sun Lee, Songpa-gu (KR); Won Young Lee, YongIn (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 54 days.

(21) Appl. No.: 14/443,246

(22) PCT Filed: Nov. 15, 2013

(86) PCT No.: PCT/KR2013/010400
§ 371 (c)(1),
(2) Date: May 15, 2015

(87) PCT Pub. No.: WO2014/077619
PCT Pub. Date: May 22, 2014

(65) Prior Publication Data
US 2015/0307681 A1   Oct. 29, 2015

(30) Foreign Application Priority Data
Nov. 16, 2012   (KR) .................. 10-2012-0130094

(51) Int. Cl.
*C08J 9/00* (2006.01)
*C08J 11/06* (2006.01)
*B09B 3/00* (2006.01)
*C08J 9/12* (2006.01)
*A61F 13/15* (2006.01)
*A61F 13/53* (2006.01)

(52) U.S. Cl.
CPC ............. *C08J 11/06* (2013.01); *B09B 3/0016* (2013.01); *A61F 13/15268* (2013.01); *A61F 2013/530481* (2013.01); *C08J 2300/14* (2013.01)

(58) Field of Classification Search
CPC .................. C08J 11/06; B09B 3/0016
USPC ............................................. 521/40
See application file for complete search history.

(56) References Cited

U.S. PATENT DOCUMENTS

| | | | |
|---|---|---|---|
| 5,292,075 A | 3/1994 | Bartlett | |
| 7,306,697 B2 | 12/2007 | Kikushima et al. | |
| 7,662,347 B2 | 2/2010 | Heidel | |
| 7,910,688 B2 | 3/2011 | Tian et al. | |
| 7,977,531 B2 | 7/2011 | Dodge, II et al. | |
| 8,177,151 B2 | 5/2012 | Grimes | |
| 2009/0191408 A1 | 7/2009 | Tian et al. | |
| 2009/0192481 A1 | 7/2009 | Dodge, II et al. | |
| 2009/0326497 A1 | 12/2009 | Schmidt | |
| 2010/0292401 A1 | 11/2010 | Grimes | |
| 2014/0024561 A1* | 1/2014 | Reddy ............. | C08J 3/245 507/117 |

FOREIGN PATENT DOCUMENTS

| | | |
|---|---|---|
| DE | 198 53 520 C2 | 5/2001 |
| JP | 2000-246011 A | 9/2000 |
| JP | 2003/225645 A | 8/2003 |
| JP | 2003-300051 A | 10/2003 |
| JP | 4685973 B1 | 5/2011 |
| KR | 10-2011-0029724 A | 3/2011 |
| KR | 10-1044439 B1 | 6/2011 |
| KR | 10-1173154 B1 | 8/2012 |
| WO | WO 92/07995 A1 | 5/1992 |
| WO | WO 99/24168 A1 | 5/1999 |
| WO | WO 2009/060893 A1 | 5/2009 |
| WO | WO 2009/081124 A2 | 7/2009 |

* cited by examiner

*Primary Examiner* — Terressa Boykin
(74) *Attorney, Agent, or Firm* — Kimberly-Clark Worldwide, Inc.

(57) ABSTRACT

The present invention relates to a method for removing water from swollen superabsorbent polymers in a gel state, and a method for recycling sanitary absorbent articles using the same. According to the method of the present invention, water is removed from swollen superabsorbent polymers by immersing swollen superabsorbent polymers in a gel state into a composition wherein sea water that is readily available and calcium chloride that is readily available at low cost are mixed for a specified period of time. The method makes it possible to easily and economically remove water from swollen SAPs in a gel state. Thus, the method provides an economical and environmentally-friendly means for recycling sanitary absorbent articles comprising an absorbent that consists of SAP and cellulose pulp, after being used for absorbing human waste.

9 Claims, 2 Drawing Sheets

METHOD FOR BELCHING WATER FROM SWOLLEN SUPERABSORBENT POLYMERS AND METHOD FOR RECYCLING SANITARY ABSORBENT ARTICLES USING THE SAME

RELATED APPLICATIONS

The present application is a national-phase entry, under 35 U.S.C. §371, of PCT Patent Application No. PCT/KR2013/010400, filed on Nov. 15, 2013, which claims priority to Korean Patent Application No. 10-2012-130094, filed on Nov. 16, 2012, all of which are incorporated herein by reference in a manner consistent with the present application.

FIELD OF THE INVENTION

The present invention relates to methods for belching water from swollen superabsorbent polymers in a gel state, and methods for recycling sanitary absorbent articles using the same. More specifically, the present invention relates to methods for easily and economically removing water absorbed by superabsorbent polymers, by immersing superabsorbent polymers in a gel state into a composition wherein readily available sea water and 0.5 to 3% by weight of inexpensive calcium chloride that is easy to handle based on the weight of sea water are mixed for 10 minutes to 4 hours; and economical and environmentally-friendly methods for recycling used sanitary absorbent articles such as diapers.

BACKGROUND OF THE INVENTION

There has been an increasing use of sanitary absorbent articles including diapers each year. Currently, all the used sanitary absorbent articles are incinerated or disposed in a landfill. However, incinerating or disposing the articles in a landfill results in problems of lack of landfill sites or problems in that incineration results in high processing cost and adversely affects the environment due to carbon dioxide produced during the process, since used sanitary absorbent articles contain moisture comprising human waste such as urine.

Further, since large quantities of materials (resources) are consumed for manufacturing sanitary absorbent articles relative to the purpose of treating human waste, there has been an increasing demand for recycling or reusing sanitary absorbent articles. Thus, there is a need for efficient and economical processes for recycling used sanitary absorbent articles into individual constituents by decomposing or isolating main constituents of the absorbent articles without harming the environment.

A technique is desirable that is capable of isolating the constituents of sanitary absorbent articles into individual resources before used sanitary absorbent articles, such as diapers, can be recycled. In general, sanitary absorbent articles, such as baby diapers, consist of polypropylene (PP), polyethylene (PE), superabsorbent polymer (SAP), cellulose pulp, and the like.

Among the main components of sanitary absorbent articles, those such as polypropylene or polyethylene which are physically bound can be easily isolated by crushing, but the absorbent prepared by mechanically mixing superabsorbent polymers and cellulose pulp in a uniform distribution having a certain arrangement cannot be isolated into individual materials mechanically or by other physical measures, because superabsorbent polymers become a gel state as they absorb moisture from human waste to be swollen (i.e., become larger in volume) and are tangled with cellulose pulp fibers.

In order to isolate such superabsorbent polymers in a gel state and cellulose pulp into individual resources, superabsorbent polymers must be converted from a gel state to the original particle state by removing moisture absorbed by superabsorbent polymers.

Thus, in order to recycle used sanitary absorbent articles having an absorbent consisting of superabsorbent polymers and cellulose pulp by isolating their constituents into individual materials, a technique should be developed that makes it easier to isolate superabsorbent polymers and cellulose pulp into individual materials by allowing moisture absorbed by superabsorbent polymers to be discharged to convert the polymers from a gel state to the original particle state.

Korea Patent Laid-Open No. 2011-0029724 discloses separating superabsorbent polymers from a pulp by using chemicals such as bittern, acetic acid and hypochlorous acid, in order to isolate constituents of the absorbent wherein water is absorbed into individual materials. However, this technique has problems in that the substances used have a very irritating odor, generate harmful gases and are not easy to handle during the separating process. Another problem is the high cost of using bittern, for which additional purification or processing is required.

Further, techniques of recycling used diapers or the like by mechanically crushing and re-extruding into low grade fuels have been known, but such techniques are uneconomical and thus are impractical.

DESCRIPTION OF THE INVENTION

Problems to be Solved by the Invention

It is an object of the present invention to solve the problems of conventional techniques as described above, and to provide methods for economically and easily removing moisture absorbed by a superabsorbent polymer, capable of absorbing an amount of moisture equivalent to a hundred times its own weight, once it has been used for its intended purpose.

It is another object of the present invention to provide environmentally-friendly and economical methods for recycling used sanitary absorbent articles comprising an absorbent consisting of a superabsorbent polymer and cellulose pulp by allowing moisture absorbed by the superabsorbent polymers to be discharged to convert the polymer from a gel state to the original state, such that the superabsorbent polymers can be easily separated from the cellulose pulp.

Means to Solve the Problems

In order to achieve the above objectives, there are provided methods for belching water from swollen superabsorbent polymers comprising immersing swollen superabsorbent polymers in a gel state into a composition for removing moisture, wherein sea water and 0.5 to 3% by weight of calcium chloride based on the weight of sea water are mixed for 10 minutes to 4 hours.

Further, the present invention provides methods for recycling sanitary absorbent articles comprising superabsorbent polymer and cellulose pulp as an absorbent, wherein moisture is absorbed by using said methods.

Effects of the Invention

According to the methods of the present invention, it is possible to easily and economically remove moisture absorbed by superabsorbent polymers with high efficiency.

Further, the methods of the present invention can be advantageously used for recycling sanitary absorbent articles comprising an absorbent consisting of superabsorbent polymer and cellulose pulp, which had been difficult to isolate into individual resources by means of conventional chemical processes, after being used for human waste treatment purposes.

DETAILED DESCRIPTION FOR PRACTICING THE INVENTION

Figure 1:
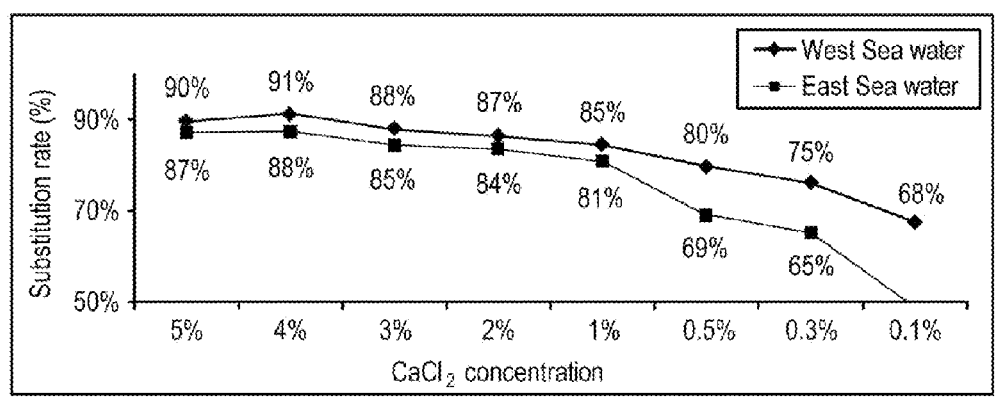
FIG. 1 is a graph showing moisture substitution (%) according to calcium chloride ($CaCl_2$) concentration of sea water.

The present invention provides methods for belching water from swollen superabsorbent polymers, and methods for recycling sanitary absorbent articles using the same.

More specifically, the present invention provides methods for belching water from swollen superabsorbent polymers in a gel state by immersing swollen superabsorbent polymers in a gel state into an aqueous solution, wherein a specified ratio of calcium chloride that is inexpensive and readily available, and sea water that is readily available and does not undergo separate purification or processing or an artificial sea water having a similar composition are mixed for a specified period of time.

The methods according to the present invention for belching water from swollen superabsorbent polymers comprise immersing swollen superabsorbent polymers in a gel state into a composition for removing moisture, wherein sea water and 0.5 to 3% by weight of calcium chloride based on the weight of sea water are mixed for 10 minutes to 4 hours.

Sanitary absorbent articles including baby diapers generally consist of lining, absorbent transport layer, absorbent, waterproof film, and leg/waist band, and the like. Further, the absorbent is composed of superabsorbent polymer material and cellulose pulp. The functions and actions of each constituent are briefly described below.

The lining directly contacts the user's skin, and passes human waste toward the absorbent as it occurs and keeps its surface dry. Further, the absorbent transport layer serves to allow the human waste transported to the absorbent after human waste passes through the lining, and to prevent the waste from returning back to the lining. In addition, the absorbent consisting of cellulose pulp and superabsorbent polymer that are capable of absorbing an amount of moisture equivalent to a hundred times its own weight is covered by polypropylene nonwoven fabrics in order to maintain its shape. The lining, waterproof film, waist band and leg band as well as the absorbent are mutually fixed via physical or chemical bonding means.

Absorptivity of the superabsorbent polymer, one of the constituents of the absorbent, is a function that increases with increased contact area between solutions to be absorbed and the polymer materials, with increased osmotic pressure due to the difference in ion concentration inside and outside the polymer material, and with increased repulsion between molecular chains in the polymer materials. The absorption is ideally reversible.

Thus, moisture absorbed by polymer materials can be expelled out, when a new outer environment is created by incorporating a solution for removing moisture that was absorbed in the superabsorbent polymer materials to create an outward osmotic flow from the inside of the polymer materials or to lower the repulsion between molecular chains in the polymer material.

Since superabsorbent polymer materials are conventionally obtained in the art by polymerization of acrylic acid and sodium hydroxide, sodium ion is contained in superabsorbent polymer molecules. Further, when contacted with moisture including human waste such as urine, artificial urine, or water, sodium ions in the polymer molecules readily dissociate to form a concentration gradient between the inside and outside of the polymer materials, thereby causing an inflow of moisture from outside the polymer materials. On the other hand, if relatively higher concentrations of sodium ions are provided outside the polymer materials, counter-flow is created to belch moisture absorbed by the polymer materials.

Further, intermolecular repulsion between superabsorbent polymer materials is induced by negative charges generated by oxidation of sodium ions comprised within the polymer molecules, and if an oxidant (e.g., a divalent metal cation) that weakens the repulsion between negative charges is present, the repulsion is weakened to decrease the distance between the molecular chains of the polymers. As a result, the space for retaining moisture becomes narrower such that moisture absorbed in the polymer materials is discharged.

Although a similar effect may also occur, when absorbent materials are under a strong acidic environment, such a process may not be an appropriate practical alternative due to the difficulties in handling, odors, etc., of the solutions to be used for recycling.

Superabsorbent polymers (SAPs) to be used in the present invention are not particularly limited, but any SAPs generally used in sanitary absorbent articles can be used. Further, they are commercially available. For the present invention, SAPs having the following properties can be used:

Appearance: white powders
pH: 5.5-6.5 (@ 5.0 g/l, 0.9% NaCl solution)
Specific gravity: 0.6-0.8 $g/cm^3$ (apparent density)
Absorptivity: 49-55 g/g
Absorptivity under pressure (0.9 psi): 19.5-21 g/g
Gel strength: 65,000-90,000 $dyne/cm^2$ In the present invention, swollen superabsorbent polymers in a gel state refer to SAPs in a gel state wherein 40 to 1,000 times of moisture based on their weight are absorbed. In order to examine their functions under similar conditions of using absorbent articles, they can be obtained by allowing SAPs to absorb moisture such as artificial urine, i.e., 0.9% by weight aqueous NaCl solution (hereinafter, referred to as "physiological saline") that is similar to human urine, or urine as real human waste, or distilled water.

In the present invention, as the sea water in the composition for removing moisture that is used for belching water from swollen superabsorbent polymers in a gel state, natural sea water can be used directly without undergoing further processing or purification, or artificial sea water having a similar composition to that of sea water can be purchased or prepared for use.

Sea water that can be used in the present invention may have a salinity (%) of 2.0 to 4.0%, and comprise 1.5 to 3.1% by weight of sodium chloride and 0.4 to 0.8% by weight of alkaline earth metal ions, such as $Mg^{2+}$ and $Ca^{2+}$.

Accordingly, based on sea water having a salinity of 3.5%, sea water comprises about 2.7% by weight of sodium chloride, which is about three times of the salinity of urine (0.9% by weight), and thus, if swollen SAPs in a gel state are immersed into an aqueous solution containing sea water, the solution serves to generate an osmotic flow from the inside to the outside of the SAP materials. Furthermore, alkaline earth metal ions, such as $Mg^{2+}$ and $Ca^{2+}$, contained in sea water interact with an anion within the swollen SAP materials in a gel state to lower the repulsion between SAP molecules. Thus, the effect of expelling moisture absorbed by the SAPs outside the molecules is further increased.

Calcium chloride used in a composition for removing moisture according to the present invention is easy to handle, readily available at low cost, has little toxicity or odor, and primarily exist as ions in an aqueous solution due to its very high degree of ionization. Commercially available calcium chloride having a purity of 74 to 99% by weight can be used as is without purification. When removing water absorbed by SAPs, using in the sea water a composition obtained by adding 0.5 to 3% by weight of calcium chloride based on the weight of sea water provides an effect of further increasing $Ca^{2+}$ concentration in addition to $Ca^{2+}$ ions contained in sea water itself. This further lowers the repulsion between anions within SAPs in a gel state, thereby making it possible to more efficiently discharge moisture absorbed by SAPs.

The aqueous solution containing sea water and calcium chloride may have a pH in a range of 7.0 to 8.0, which is desirable since the efficiency of belching water from swollen superabsorbent polymers in a gel state is high within this range.

Thus, according to the methods of the present invention wherein swollen superabsorbent polymers in a gel state are immersed into a mixed aqueous solution comprising natural sea water that is readily available without further processing or purification and calcium chloride that is available at low cost and has little toxicity or smell, it is possible to easily and economically remove moisture absorbed by superabsorbent polymers at a high substitution rate of 80 to 90%.

The methods according to the present invention can be advantageously used as an environmentally-friendly and economical means to recycle sanitary absorbent articles, including baby diapers, comprising an absorbent that consist of SAP and cellulose pulp, after the article has been used for absorption.

The present invention is further described and illustrated according to the examples provided below. However, it should be noted that the following examples are presented only for illustrative purposes and are not intended to limit the scope of the present invention.

Experimental Example

Moisture substitution rate from superabsorbent polymers in a gel state, which had been swollen by physiological saline having a similar composition to that of urine, was determined by carrying out substitution procedures as described below.

1. 100 g of physiological saline per 1 g of superabsorbent polymers (SAP) is added to SAP (SAP GS 4700, LG Chem.), and the polymer is allowed to sufficiently absorb moisture for 40 minutes.
2. Unabsorbed physiological saline is removed therefrom by using a 300 μm mesh to obtain the swollen SAP sample in a gel state. At this point, in the case of physiological saline, superabsorbent polymers absorb about 43 to 50 times by weight of moisture based on the their weight to obtain about 43 to 50 g of superabsorbent polymers in a gel state per 1 g of SAP.
3. The swollen SAP sample is immersed into each composition for removing moisture (about twice by weight of swollen SAP), and kept for 40 minutes for reaction.
4. After the reaction is completed, remaining swollen SAP is filtered through a 300 μm mesh, and the amount of filtrate containing moisture that is substituted is measured.
5. The absorptivity (g/g) before/after the substitution is calculated to obtain the moisture substitution rate.

Example 1

Substitution Effect for Individual Main Components of Sea Water

In order to determine the substitution effect for individual main components of sea water, the main components of artificial sea water were examined (see, http://en.wikipedia.org/wiki/Artificial_sea water), as summarized in Table 1.

TABLE 1

| Component | Content (wt %) | Component | Content (wt %) |
|---|---|---|---|
| Sodium chloride (NaCl) | 2.4 | Boric acid ($H_3BO_3$) | 0.0026 |
| Sodium sulfate ($Na_2SO_4$) | 0.4 | Sodium fluoride (NaF) | 0.0003 |
| Potassium chloride (KCl) | 0.7 | Magnesium chloride hexahydrate ($MgCl_2 \cdot 6H_2O$) | 1.1 |
| Sodium hydrogen carbonate ($NaHCO_3$) | 0.02 | Calcium chloride dihydrate ($CaCl_2 \cdot 2H_2O$) | 0.2 |
| Potassium bromide (KBr) | 0.01 | Strontium chloride hexahydrate ($SrCl_2 \cdot 6H_2O$) | 0.0024 |

The substitution experiment for Experimental Example 1 was carried out by using 100 g of physiological saline in step 1 of the above Experimental Example, and by using aqueous solutions of each component having said concentrations and using sea water as a composition for removing moisture with a reaction time of 10 minutes. Absorptivity (g/g) of swollen SAP in a gel state before substitution, and absorptivity (g/g) of SAP after substitution were determined respectively, and the results are shown in Table 2.

TABLE 2

| | Component | | | | |
|---|---|---|---|---|---|
| | Artificial sea water | 2.4 wt % aqueous solution of sodium chloride | 0.4 wt % aqueous solution of sodium sulfate | 0.07 wt % aqueous solution of potassium chloride | 0.02 wt % aqueous solution of sodium hydrogen carbonate | 0.01 wt % aqueous solution of potassium bromide |
| Before substitution (g/g) | 44.4 | 43.1 | 43.1 | 43.1 | 43.1 | 43.1 |
| After substitution (g/g) | 10.5 | 18.8 | 24.6 | 26.4 | 26.7 | 28.1 |

| | Component | | | | |
|---|---|---|---|---|---|
| | 0.0026 wt % aqueous solution of boric acid | 0.0003 wt % aqueous solution of sodium fluoride | 1.1 wt % aqueous solution of magnesium chloride | 0.2 wt % aqueous solution of calcium chloride | 0.0024 wt % aqueous solution of strontium chloride | — |
| Before substitution (g/g) | 43.1 | 43.1 | 43.1 | 43.1 | 43.1 | — |
| After substitution (g/g) | 28.5 | 25.8 | 13.7 | 18.5 | 22.5 | — |

As a result of determining the substitution rate for individual main components that are isolated from sea water, Table 2 shows that among the constituents of sea water, the effect of removing moisture from swollen SAPs in a gel state is particularly imparted by sodium chloride, magnesium chloride and calcium chloride.

Example 2

Substitution Effect According to Salinity of Sea Water, Concentration of Calcium Chloride, and Reaction Time East sea water was taken from the seashore of Joyang-dong, Sokcho-shi, Gangwon-do, and West sea water was taken from the seashore of Youngjong-do, Incheon. Elemental analysis was carried out by the Korea Testing and Research Institute (KTR) upon request, and the results are shown in Table 3.

TABLE 3

| Salinity | F | Cl | $SO_4$ | Br | $HCO_3$ | Na | Mg | Ca | K | B | Sr | Salinity (%) |
|---|---|---|---|---|---|---|---|---|---|---|---|---|
| East Sea | 0.89 | 19300 | 2750 | 69.8 | 216 | 10100 | 1200 | 353 | 360 | 4.15 | 7.92 | 32.2 |
| West Sea | 0.73 | 13100 | 1910 | 50.4 | 189 | 6700 | 776 | 236 | 235 | 3.10 | 5.53 | 22.0 |

To the sea water from East Sea and West Sea, calcium chloride was respectively added to obtain mixed aqueous solutions having a concentration of 0.1 to 5% by weight. By using the mixed aqueous solutions as a composition for removing moisture from the swollen SAP sample, Experimental Example 1 was carried out (provided that reaction time in step 3 was 10 minutes), and the moisture substitution rate according to the concentration of calcium chloride was determined and shown in FIG. 1.

Further, by using an aqueous solution wherein sea water and 0.5% by weight of calcium chloride based on the weight of sea water are mixed as a composition for removing moisture from the swollen SAP sample, the moisture substitution rate was determined with the reaction time in step 3 changed to 10-60 minutes. The results are shown in FIG. 2.

Figure 2:
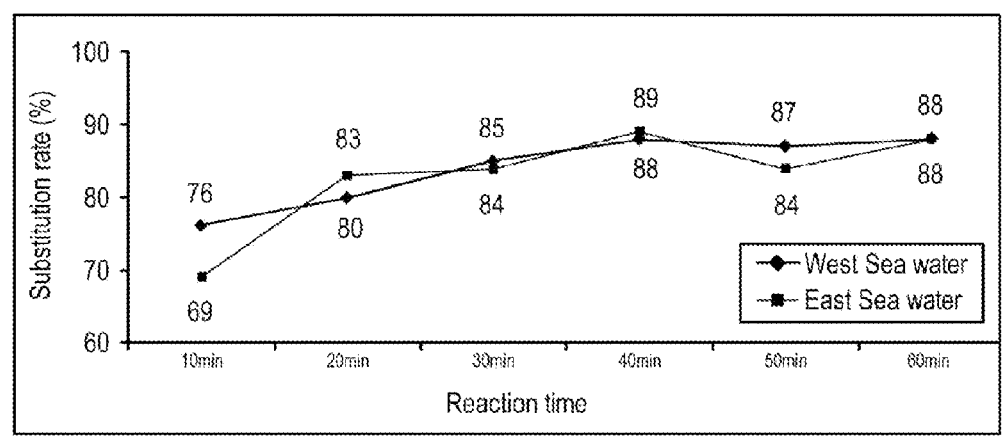
FIG. 2 is a graph showing moisture substitution (%) according to reaction time with sea water.

As can be seen from FIGS. 1 and 2, the moisture substitution effect is higher for East Sea water having a higher salinity of 3.2% as compared to West Sea water having a lower salinity of 2.2%, and such difference in substitution efficiency resulting from the difference in salinity could be complemented by the reaction time for substitution. In addition, since the difference in substitution efficiency due to the difference in constituents including salinity can be complemented by the reaction time, sea water having a salinity of about 2.0% to 4.0% may be used as a composition for removing moisture from the swollen SAP samples.

Example 3

Substitution Effect of Other Materials

Figure 3:
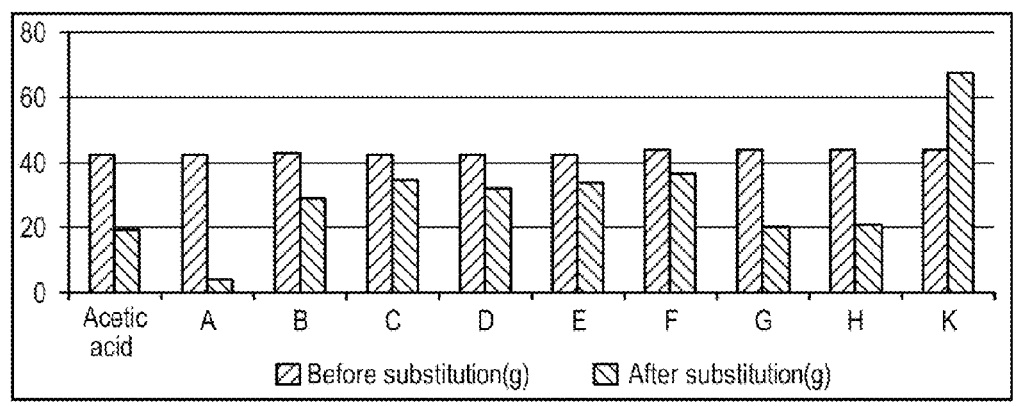
FIG. 3 is a graph showing moisture substitution (%) according to the use of different compositions for removing moisture.

Experimental Example was carried out by using 5% by volume aqueous solution of acetic acid and aqueous solutions as shown below (A to K) as a composition for removing moisture from SAPs in a gel state, wherein artificial urine (physiological saline) are absorbed, with a reaction time of 40 minutes. Absorptivity (g/g) of SAP in a gel state before substitution, wherein artificial urine is absorbed, and absorptivity (g/g) of the same after substitution were determined, respectively, to test the substitution effects of various substances. The results are shown in Table 4 and FIG. 3.

TABLE 4

| | Component | | | | | | | | | |
|---|---|---|---|---|---|---|---|---|---|---|
| | Acetic acid | A | B | C | D | E | F | G | H | K |
| Before substitution (g/g) | 42.5 | 42.5 | 43.0 | 42.5 | 42.5 | 42.5 | 44.0 | 44.0 | 44.0 | 44.0 |
| After substitution (g/g) | 20.0 | 4.0 | 29.0 | 35.0 | 32.0 | 34.0 | 37.0 | 20.0 | 21.0 | 68.0 |

A: 5% by weight aqueous solution of calcium chloride ($CaCl_2$)
B: 5% by weight aqueous solution of sodium chloride (NaCl)
C: 5% by weight aqueous solution of sodium sulfate ($Na_2SO_4$)
D: 5% by weight aqueous solution of potassium chloride (KCl)
E: 5% by weight aqueous solution of sodium hydrogen carbonate ($NaHCO_3$)
F: 5% by weight aqueous solution of potassium bromide (KBr)
G: East Sea water
H: West Sea water
K: Distilled water As can be seen in Table 4 and FIG. 3, the substitution rate was as low as 54% where 5 wt % aqueous solution of acetic acid was used as a composition for removing moisture from swollen SAPs in a gel state, while the substitution rate was as high as 90% where 5 wt % aqueous solution of calcium chloride was used, which shows an excellent effect of removing moisture from swollen SAPs. Further, in the case of sea water (G and H), the effect of substitution by artificial urine is somewhat lower than that of calcium chloride, but the substitution effect was substantially the same in the case of acetic acid (52-54%). In addition, it was evident that substitution with water occurred where swollen SAPs absorbed artificial urine, whereas substitution by water was not possible in the case of K (distilled water).

Example 4

Substitution Effect According to a Concentration of Calcium Chloride

Experimental Example 1 was carried out by using 0.5 to 5% by weight aqueous solution of calcium chloride or 0.5% by weight aqueous solution of calcium chloride in East Sea water as a composition for removing moisture from SAPs in a gel state wherein artificial urine is absorbed. Absorptivity (g/g) of SAPs in a gel state before substitution wherein artificial urine is absorbed, and absorptivity (g/g) of the same after substitution were determined, respectively, to test the substitution effects for each solution. The results are shown in Table 5 and FIG. 4.

TABLE 5

| | Concentration of calcium chloride | | | | |
|---|---|---|---|---|---|
| | 5% | 2% | 1% | 0.5% | 0.5% + sea water |
| Before substitution (g/g) | 42.5 | 42.5 | 43.0 | 43.5 | 43.5 |
| After substitution (g/g) | 4.0 | 6.0 | 15.0 | 37.0 | 8.0 |
| Substitution rate (%) | 90.6 | 85.9 | 65.1 | 14.9 | 81.6 |

Figure 4:
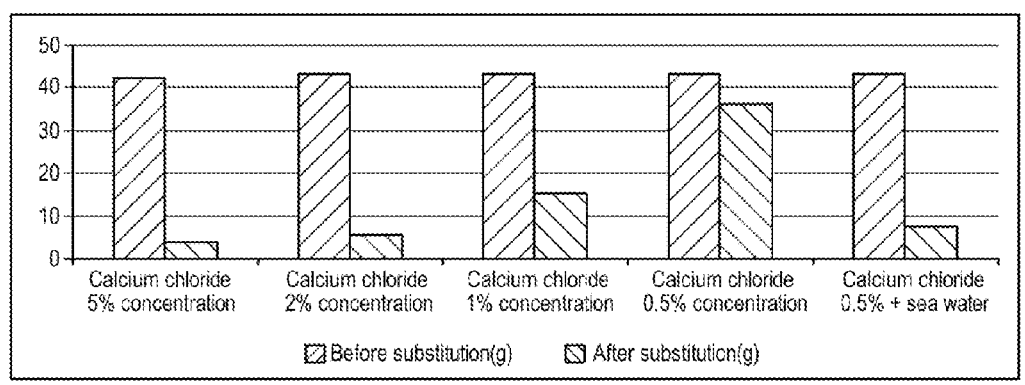
FIG. 4 shows a graph showing moisture substitution (%) according to calcium chloride ($CaCl_2$) concentrations.

From the results shown in Table 5 and FIG. 4, it is evident that in the case of using aqueous solution of calcium chloride for removing moisture from SAPs in a gel state wherein artificial urine is absorbed, at least 2% by weight of calcium chloride should be used in order to provide a moisture substitution rate of 80% or more, while in the case of using sea water instead of water in aqueous solution of calcium chloride (in other words, in the case of using aqueous solution wherein sea water and calcium chloride are mixed), a calcium chloride concentration as low as 0.5% by weight can provide a high substitution rate of 80% or more. Thus, it is economically advantageous to use an aqueous solution in which sea water and calcium chloride are mixed for removing moisture from swollen SAPs in a gel state.

Example 5

Effect of Recovering Raw Materials

A recovery test was carried out as follows in order to determine the rate of recovery of cellulose and SAP raw materials, respectively, after using the method according to the present invention for removing moisture absorbed in SAP from an absorbent consisting of cellulose and SAP by using an aqueous solution wherein sea water and calcium chloride (concentration: 0.5 to 3 wt %) are mixed.

5 g of fluff pulp (GP4860, Georgia-Pacific), generally used in absorbent articles, is prepared.

10 g of SAP (SAP GS 4700, LG Chem.), generally used in absorbent articles, is prepared.

Said fluff pulp is put into a beaker and 600 cc of physiological saline is added thereto, followed by stirring.

Said SAP is mixed therewith and stirred, followed by allowing the SAP to sufficiently absorb moisture for 40 minutes to become a gel state.

Residual physiological saline after absorption is removed therefrom, and then 1500 cc of the composition shown in Table 5 is added thereto, followed by substitution for 40 minutes to 4 hours.

After the reaction has completed, fluff pulp is isolated therefrom by using a 1.18 mm mesh.

SAP is isolated therefrom by using a 300 μm mesh.

Each isolated sample is dried in a drier at 105 to 110° C. for at least 12 hours, their weights before/after drying are measured to determine initial amount of SAP added and recovered amount of SAP, and then SAP recovery rates (%) are calculated therefrom.

As described above, SAP recovery rates (%) were determined by removing water from the absorbent in a gel state using a composition according to the present invention after artificially swelling SAP and cellulose pulp in physiological saline, in conditions similar to that of actual use of absorbent articles. The results are shown in Table 6.

TABLE 6

| No. | Initial amount of SAP (g) | Recovered amount of SAP (g) | Recovery rate (%) | Condition of composition | Reaction time (min) | Used sea water |
|---|---|---|---|---|---|---|
| 1 | 10.00 | 7.94 | 79.4 | $CaCl_2$ 0.5% + sea water | 40 | East Sea |
| 2 | 10.00 | 8.36 | 83.6 | $CaCl_2$ 0.5% + sea water | 60 | West Sea |
| 3 | 10.00 | 7.33 | 73.3 | $CaCl_2$ 1.0% + sea water | 40 | East Sea |
| 4 | 10.00 | 7.78 | 77.8 | $CaCl_2$ 1.0% + sea water | 60 | West Sea |
| 5 | 10.00 | 9.12 | 91.2 | $CaCl_2$ 3.0% + sea water | 60 | East Sea |
| 6 | 10.00 | 8.52 | 85.2 | $CaCl_2$ 3.0% + sea water | 60 | West Sea |

As can be seen from Table 6, SAP recovery rates (%) increase with the increase of concentration of calcium chloride, reaction time, and salinity of sea water.

What is claimed is:

1. A method for belching water from superabsorbent polymers (SAPs) swollen with water from human waste, the method comprising:
    immersing the water-swollen SAP in a gel state, taken from a sanitary absorbent article, into a composition for removing the human-waste-based water, wherein the composition includes sea water and 0.5 to 3% by weight of calcium chloride based on the weight of sea water.

2. The method according to claim 1, wherein the swollen SAP in a gel state absorbs 40 to 1,000 g of moisture per 1 g of SAP.

3. The method according to claim 1, wherein the sea water is natural sea water that does not undergo further processing or purification, or artificial sea water.

4. The method according to claim 1, wherein the sea water comprises 2.0 to 4.0% by weight of salts based on the total weight of sea water.

5. The method according to claim 4, wherein the sea water comprises 1.5 to 3.1% by weight of sodium chloride and 0.4 to 0.8% by weight of alkaline earth ion, based on the total weight of sea water.

6. The method according to claim 1, wherein the composition for removing moisture has a pH ranging from 7.0 to 8.0.

7. A method for recycling sanitary absorbent articles wherein water from human waste is removed using the method according to claim 1.

8. The method according to claim 7, wherein the sanitary absorbent article comprises an absorbent consisting of superabsorbent polymer and cellulose pulp.

9. The method according to claim 8, wherein the sanitary absorbent article is a diaper.

* * * * *